United States Patent [19]
Kraske

[11] Patent Number: 5,842,990
[45] Date of Patent: Dec. 1, 1998

[54] STEREOTACTIC ULTRASONIC DIAGNOSTIC PROCESS

[75] Inventor: Wolfgang Frederick Kraske, Whittier, Calif.

[73] Assignee: Northrop Grumman Corporation, Los Angeles, Calif.

[21] Appl. No.: 916,937

[22] Filed: Aug. 21, 1997

[51] Int. Cl.[6] ........................................................ A61B 8/00
[52] U.S. Cl. ............................................ 600/437; 606/130
[58] Field of Search ..................................... 600/437, 417, 600/439, 459, 461, 464, 471; 606/130

[56] References Cited

U.S. PATENT DOCUMENTS

| | | | |
|---|---|---|---|
| 3,439,530 | 4/1969 | Flaherty et al. | 73/67.8 |
| 4,545,385 | 10/1985 | Pirschel | 128/660 |
| 4,592,352 | 6/1986 | Patil | 128/303 |
| 4,608,977 | 9/1986 | Brown | 128/303 |
| 4,681,103 | 7/1987 | Bones et al. | 600/461 |
| 4,951,653 | 8/1990 | Fry et al. | 601/2 |
| 5,078,140 | 1/1992 | Kwoh | 600/417 |
| 5,099,846 | 3/1992 | Hardy | 600/417 |
| 5,213,100 | 5/1993 | Summ | 128/653.1 |
| 5,221,283 | 6/1993 | Chang | 606/130 |
| 5,246,448 | 9/1993 | Chang | 606/130 |
| 5,514,146 | 5/1996 | Lom et al. | 606/130 |
| 5,647,373 | 7/1997 | Paltieli | 600/459 |

*Primary Examiner*—Francis J. Jaworski
*Attorney, Agent, or Firm*—Terry J. Anderson; Karl J. Hoch, Jr.

[57] ABSTRACT

A method of locating diseased intracranial tissue employing ultrasonic imaging. The method includes providing a stereotactic frame having a plurality of frame members in a plurality of planar orientations. An ultrasonic probe device in communication with a computed tomography scanner is mounted on a frame member, and the frame is secured to a skull of a living being such that the probe device is aimed toward the skull. The probe is activated at a plurality of sites on the frame member, and respective scan slice images corresponding to each of the plurality of sites from within the skull are recorded. The method can also include employment of at least one additional probe device chosen from the group consisting of a magnetic resonance imaging probe, a positron tomography emission probe and an x-ray computed tomography probe. Each device is similarly mounted on a frame member and activated in sequence with the ultrasonic probe at the plurality of sites where activation of the ultrasonic probe occurs such that images captured by each additional device during such activation are recorded.

7 Claims, 1 Drawing Sheet

STEREOTACTIC ULTRASONIC DIAGNOSTIC PROCESS

FIELD OF THE INVENTION

This invention relates in general to methodology for medical diagnoses, and in particular to a method of locating diseased intracranial tissue through use of a skull-secured stereotactic frame upon which is mounted an ultrasonic probe in communication with a computed tomography scanner, and thereafter activating the probe at a plurality of sites and recording respective scan slice images corresponding to each of said plurality of sites from within the skull.

BACKGROUND OF THE INVENTION

Employment of stereotactic medical procedures in conjunction with computer tomography (CT) systems is an accepted approach in the diagnosis of intracranial disease. Briefly, such a procedure includes a stereotactic frame which is a structure having a plurality of frame members with measurement markers thereon and upon which various devices can be movably attached for measured movement and placement in a plurality of planes. The frame is mountable on the skull of a patient, and is provided with reference land mark s such that frame placement as well as device placement on frame members can be duplicated as needed in the treatment of the patient. One example of a stereotactic frame is found in U.S. Pat. No. 4,608,977, to Brown.

At the present time, devices mounted on stereotactic frame members include those that function to provide magnetic resonance imaging, positron emission tomography and x-ray computed tomography, all functioning to provide scan slice images of tissue that subsequently are reassembled electronically to produce a visual image of the injured or diseased site. Conversely, ultrasound diagnostic techniques teach only the placement of an ultrasonic probe against a patient's skull. Thus, stereotactic diagnostic procedures incorporating ultrasound diagnostic capabilities have not been recognized or suggested as a primary or a supplemental diagnostic tool for diseases of the brain.

In view of the importance of vigorous and aggressive diagnosis of diseases of the brain, it is apparent that a need is present to employ all effective diagnostic methodologies in the treatment of neurological diseases. Accordingly, a primary object of the present invention is to provide a stereotactic method of locating diseased intracranial tissue through employment of an ultrasound probe device mounted on a stereotactic frame and activated at a plurality of sites to record respective scan slice images of the brain.

Another object of the present invention is to provide a stereotactic method of locating diseased intracranial tissue by activating an ultrasound probe mounted on a stereotactic frame at a plurality of sites in a plurality of planes and correlating respective scan slice images.

These and other objects of the present invention will become apparent throughout the description thereof which now follows.

SUMMARY OF THE INVENTION

The present invention is a method of locating diseased intracranial tissue employing ultrasonic imaging. The method comprises providing a stereotactic frame having a plurality of frame members in a plurality of planar orientations, with the frame members having thereon measurement markings for duplication of location. An ultrasonic probe device in communication with a computed tomography scanner is mounted on a frame member, and the frame is secured to a skull of a living being such that the probe device is aimed toward the skull. Thereafter, the probe is activated at a plurality of sites on the frame member and respective scan slice images corresponding to each of said plurality of sites from within the skull are recorded. A medical professional can subsequently study the recorded images for diagnostic input in treating the patient.

The method can also include employment of at least one additional device chosen from the group consisting of a magnetic resonance imaging device, a positron tomography emission device and an x-ray computed tomography device. Each device is similarly mounted on a frame member of the stereotactic frame mounted on the skull of a patient and is activated in sequence with the ultrasonic probe at the plurality of sites where activation of the ultrasonic probe occurs such that images captured by each additional device during such activation are recorded. In this manner, one set of frame coordinates can be used for all activation and recordation procedures of a plurality of diagnostic devices to thereby have an alignment of images from all recordations and a consequent fused visualization of a target site to be studied for diagnosis and treatment.

BRIEF DESCRIPTION OF THE DRAWINGS

An illustrative and presently preferred embodiment of the invention is shown in the accompanying drawings in which.

DETAILED DESCRIPTION OF THE PREFERRED EMBODIMENT

Figure 1:
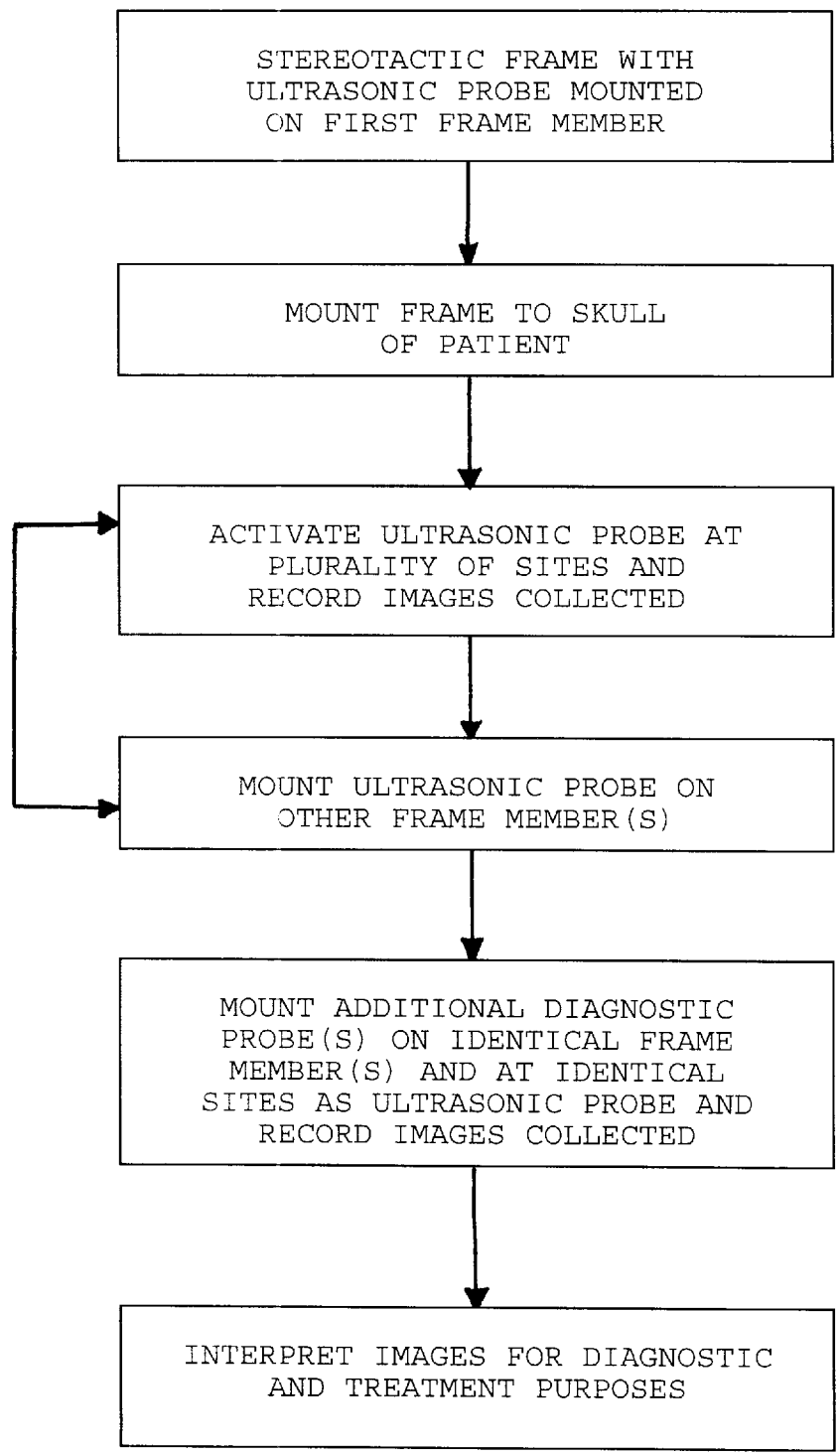
FIG. 1 is a flow sheet illustrating diagnostic methodology employing an ultrasonic probe mounted on a stereotactic frame.

Referring to FIG. 1, a flow diagram showing a diagnostic procedure performed in accord with the present invention, a stereotactic frame is provided with a conventional ultrasonic probe mounted to a frame member such that the probe will be aimed toward the skull of a patient when the frame is mounted on the patient's skull. The ultrasonic probe is first mounted on a frame member exhibiting a travel path which will encircle the skull in one planar dimension when the frame is mounted on the skull. The probe is in communication with a standard scanner.

In order to accomplish diagnostic activity, the stereotactic frame is mounted on the skull of the patient in a standard manner and the ultrasonic probe is positioned to begin image capture in accord with a physician's site choice for diagnostic procedures. After such positioning, the ultrasonic probe is activated at a plurality of sites on the frame member to thereby capture and record respective scan slice images corresponding to each of the plurality of sites. As may be required for diagnostic completion, the ultrasonic probe can be relocated to one or more other frame members having different planar orientations, and image capture and recordation can be performed in the same manner. Optionally, the physician may employ one or more additional diagnostic probe devices each in communication with a respective scanner and including, but not limited to, a magnetic resonance imaging probe device, a positron tomography emission probe device and an x-ray computed tomography probe device. When so chosen, the additional probe devices are placed at the same sites of image capture accomplished by the ultrasonic probe to thereby enhance diagnostic abilities with two or more image collections of identical sites by different devices.

As is apparent, employment of an ultrasonic probe in combination with a stereotactic frame permits collection of image data through an infinite number of cranial sites. Once these images are collected, the physician can view them to accurately estimate size and location of diseased tissue to thereby enhance accuracy in a surgical treatment procedure.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A method of locating diseased intracranial tissue comprising:
   a) providing a stereotactic frame having a plurality of stereotactic frame members in a plurality of planar orientations, said stereotactic frame members having thereon measurement markings for duplication of location;
   b) mounting an ultrasonic probe device on a stereotactic frame member, said probe device being in communication with a scanner;
   c) securing the stereotactic frame to a skull of a living being such that the probe device is aimed toward the skull; and
   d) activating the probe device at a plurality of sites on the stereotactic frame member and recording respective scan slice images corresponding to each of said plurality of sites from within the skull.

2. A method as claimed in claim 1, additionally comprising:
   a) sequentially mounting the probe device on more than one of the plurality of stereotactic frame members; and
   b) activating the probe device at a plurality of sites on each of the stereotactic frame members on which the probe device is mounted and recording respective scan slice images corresponding to each of said plurality of sites from within the skull.

3. A method as claimed in claim 1, additionally comprising sequentially mounting on the stereotactic frame member at least one additional probe device.

4. A method as claimed in claim 3 wherein the additional probe device is chosen from the group consisting of a magnetic resonance imaging probe device, a positron tomography emission probe device and an x-ray computed tomography probe device.

5. A method of locating diseased intracranial tissue comprising:
   a) providing a stereotactic frame having a plurality of stereotactic frame members in a plurality of planar orientations, said stereotactic frame members having thereon measurement markings for duplication of location;
   b) mounting an ultrasonic probe device on a stereotactic frame member, said probe device being in communication with a scanner;
   c) sequentially mounting on the stereotactic frame member at least one additional probe device;
   d) securing the frame to a skull of a living being such that the probe device is aimed toward the skull; and
   e) activating the probe device at a plurality of sites on the stereotactic from member and recording respective scan slice images corresponding to each of said plurality of sites from within the skull.

6. A method as claimed in claim 5 additionally comprising:
   a) sequentially mounting the probe device on more than one of the plurality of stereotactic frame members; and
   b activating the probe device at a plurality of sites on each of the stereotactic frame members on which the probe device is mounted and recording respective scan slice images corresponding to each of said plurality of sites from within the skull.

7. A method as claimed in claim 5 wherein the additional probe device is chosen from the group consisting of an ultrasonic probe device, a magnetic resonance imaging probe device, a position tomography emission probe device and an x-ray computed tomography probe device.

* * * * *